United States Patent [19]

Allandrieu et al.

[11] Patent Number: 5,670,689
[45] Date of Patent: Sep. 23, 1997

[54] PROCESS FOR THE MANUFACTURE OF CYCLOSILOXANES BY DEPOLYMERIZATION OF POLYSILOXANES

[75] Inventors: Christian Allandrieu; Denis Cardinaud, both of Villeurbanne, France

[73] Assignee: Rhone-Poulenc Chimie, Courbevoie Cedex, France

[21] Appl. No.: 644,277

[22] Filed: May 10, 1996

[30] Foreign Application Priority Data

May 11, 1995 [FR] France .................. 95 05570

[51] Int. Cl.⁶ .................................. C07F 7/08
[52] U.S. Cl. ............... 556/460; 556/462; 556/461
[58] Field of Search .................. 556/460, 462, 556/461

[56] References Cited

U.S. PATENT DOCUMENTS

| | | | |
|---|---|---|---|
| 5,282,998 | 2/1994 | Horn et al. | 556/460 X |
| 5,420,325 | 5/1995 | Razzano | 556/460 |
| 5,491,249 | 2/1996 | Kostas | 556/460 |

FOREIGN PATENT DOCUMENTS

| | | |
|---|---|---|
| 0523323 | 4/1992 | European Pat. Off. . |
| 0604112 | 12/1993 | European Pat. Off. . |
| 2252347 | 11/1974 | France . |
| 1618802 | 1/1966 | Germany . |

OTHER PUBLICATIONS

Journal of the American Chemical Society, vol. 68, No. 4, Apr. 1946, DC US pp. 667–672.

*Primary Examiner*—Paul F. Shaver
*Attorney, Agent, or Firm*—Burns, Doane, Swecker & Mathis, L.L.P.

[57] ABSTRACT

The present invention relates to a process for the manufacture of cyclic polydiorganosiloxanes, especially octamethylcyclotetrasiloxane ($D_4$) and decamethylcyclopentasiloxane ($D_5$) by depolymerization of polydiorganosiloxanes in the presence of an initiator, characterized in that the initiator comprises either:

1) at least one hydroxide chosen especially from the group made up of caesium, rubidium or quaternary phosphonium hydroxides, or:
2) the association of a fluorine-free caesium or rubidium salt, or of a salt of quaternary phosphoniums, with a hydroxyl-containing strong base of an alkali or alkaline-earth metal other than Cs and Rb.

26 Claims, No Drawings

PROCESS FOR THE MANUFACTURE OF CYCLOSILOXANES BY DEPOLYMERIZATION OF POLYSILOXANES

BACKGROUND OF THE INVENTION

1. Field of the Invention

The present invention relates to a process for the manufacture of cyclic polydiorganosiloxanes (PDOSs) by depolymerization of polydiorganosiloxanes.

2. Description of the Prior Art

The first stage of the manufacture of silicones conventionally includes the manufacture of chlorosilanes, especially methylchlorosilanes, by catalytic reaction of silicon and methylchloride. In a second stage the chlorosilanes obtained are hydrolyzed to obtain siloxanes. This stage in fact results in the formation of a mixture of cyclic polydiorganosiloxanes and of various linear polydiorganosiloxanes of various molecular masses.

It is advantageous to prepare silicones, especially PDOS oils, by polymerization of cyclic PDOSs such as octamethylcyclotetrasiloxane and decamethylcyclopentasiloxane (also called $D_4$ and $D_5$). In order to make such cyclic PDOSs available it is necessary to depolymerize linear PDOSs, which produces cyclic PDOSs and linear PDOSs which are shorter than the starting ones and to distil the cyclic PDOSs thus formed to isolate them. The depolymerization and distillation operations can be simultaneous or successive. These reactions are performed at elevated temperature.

Many initiators have already been employed for depolymerizing polysiloxanes.

Thus, acidic catalysts have been employed, especially in a stationary bed, for the depolymerization of polyalkylhydrosiloxanes (U.S. Pat. No. 4,895,967). These processes require elevated temperatures.

In the case of the depolymerization of polydiorganosiloxanes it has already been envisaged to employ, as initiators, alkali metal hydroxides (J. M. Hunter, J.A.C.S., 1946, 667) such as sodium hydroxide, potassium hydroxide or lithium hydroxide, alkaline-earth hydroxides, alkali metal fluorides or else mixtures of these hydroxides and fluorides. Thus, Soviet Patent 939 445 envisages a depolymerization of polydiorganosiloxanes in the presence of one of the following hydroxides: KOH, NaOH, LiOH and optionally in association with KF.

Soviet Patent 683 206 also describes the use of sodium, potassium, cesium and lithium fluoride, as well as potassium carbonate, it being possible for these salts to be employed on their own or as a mixture with various alkali or alkaline-earth metal hydroxides.

These known alkaline initiators permit reactions at temperatures which are generally low for example, between 130° and 250° C. The low temperatures are permitted by the use of the fluoride, but these initiators are not free from disadvantages, as will be seen later.

Attempts have already been made to improve some basic initiators using different adjuvants, for example use of solvents such as mineral oils, aromatic hydrocarbons or ethers or of complexing agents for the cation such as crown ethers, sequestrants and cryptands. The association of a basic initiator and crown ether is, for example, described by T. A. Koshkina et al., Russian Journal of Applied Chemistry, Vol. 66, No. 7, 1993, 1313–1314, who teach that, in the absence of such adjuvants, fluorides, acetates and carbonates have a catalytic activity close to that of sodium hydroxide, that is to say weak.

However, these adjuvants can give rise to disadvantages, in particular with regard to the viscosity of the reaction mass, the toxicity of the materials used or produced or else of the contamination due to an insufficient stability, as well as with regard to the cost of production.

The alkali metal hydroxides which have been described or employed as initiators are not fully satisfactory, especially on an industrial scale. Alkali metal fluorides are currently described as effective additives to the hydroxides. The fluoride anion is furthermore known for its nucleophilic attack on the silicon atom, with the result that it has also been recommended for the manufacture of silicones by polymerization of cyclic PDOSs.

However, the high reactivity of the materials which are present during the catalytic depolymerization process easily gives rise to undesirable secondary reactions. Thus, for example, water which may be brought in by the hydroxides promotes the formation of methane and of trifunctional units. Fluorides can give rise to compounds containing a fluorine-silicon bond, which limit the cyclization yield. Finally, the temperature conditions of the depolymerization are equally critical because they also control the extraction of the cyclic PDOSs which are formed and greatly influence the output efficiency and the quality of the latter, especially the cyclic PDOSs of $D_4$ and $D_5$ type which are particularly sought after.

SUMMARY OF THE INVENTION

The present invention proposes to overcome these disadvantages and to provide a process for depolymerization of PDOS to form cyclic PDOSs, in which the kinetics of the depolymerization of the PDOSs are increased, which makes it possible, at a given temperature, to increase output efficiency or to work at lower temperature in the case of a given output efficiency.

Another object of the invention is to obtain an increase in the selectivity for cyclic PDOSs of $D_4$ and $D_5$ type at the expense of $D_3$ (hexamethylcyclotrisiloxane), which is of little industrial interest.

Another objective of the invention is to provide such a process enabling cyclic PDOSs, especially $D_4$ and $D_5$, to be obtained in a high purity and free from SiH groups or from trifunctional units.

DETAILED DESCRIPTION OF THE PREFERRED EMBODIMENTS OF THE INVENTION

The subject-matter of the present invention is a process for the manufacture of cyclic polydiorganosiloxanes (PDOSs) and in particular of octamethylcyclotetrasiloxane ($D_4$) and of decamethylcyclopentasiloxane ($D_5$) by depolymerization of polydiorganosiloxanes (PDOSs), in the presence of an initiator, characterized in that the initiator comprises either:

1. at least one hydroxide chosen especially from the group made up of cesium, rubidium or quaternary phosphonium hydroxides, or:
2. the association of a fluorine-free cesium or rubidium salt, or of a salt of quaternary phosphoniums, with a hydroxyl-containing strong base of an alkali or alkaline-earth metal other than Cs and Rb.

The cesium, rubidium or quaternary phosphonium hydroxidesmay advantageously also be used in association with a hydroxyl-containing strong base of an alkali or alkaline-earth metal other than Cs and Rb.

The abovementioned various derivatives may, of course, be mixed with each other.

The metal derivative is preferably chosen from the group made up of cesium hydroxide or of the association between a cesium hydroxide and/or a fluorine-free cesium salt and/or a quaternary phosphonium salt and a hydroxyl-containing strong base of an alkali or alkaline-earth metal other than Cs and Rb.

The cesium or rubidium salts are preferably fluorine-free halides, especially chloride and bromide. They may also, but less preferably, be carbonates, carboxylates, phosphates, nitrates, sulphates or other salts.

The fluorine-free cesium salt is preferably chosen from the group made up of cesium chloride, bromide and carboxylate.

The cationic part of the quaternary phosphonium salts preferably corresponds to the formula (I):

in which the groups R1, R2, R3 and R4 denote identical or different, optionally substituted hydrocarbon radicals whose free valency is carried by a carbon atom.

The hydrocarbon radicals are preferably chosen from the group made up of linear or branched alkyl, cycloalkyl or aromatic radicals, especially of aryl or arylaliphatic type, it being possible for each of these radicals to be substituted by one or more halogen atom(s) or $NO_2$ or CN group(s).

The total number of carbon atoms carried by the said radicals is advantageously smaller than or equal to 50 and preferably between 6 and 30.

The quaternary phosphonium salts are halides, optionally fluorides, but preferably chlorides or bromides.

The hydroxyl-containing strong base of an alkali or alkaline-earth metal other than Cs and Rb is advantageously chosen from the group made up of potassium hydroxide, sodium hydroxide and lithium hydroxide.

The quantity of cesium, rubidium or quaternary phosphonium hydroxide per 100 g of starting PDOS subjected to the depolymerization reaction is preferably between 3 and 100 mmol and preferably between 10 and 50 mmol.

In association, the quantity of cesium, rubidium or quaternary phosphonium hydroxide and/or salt per 100 g of starting PDOS is preferably between 3 and 50 mmol, preferably between 4 and 20 mmol, and the quantity of hydroxyl-containing strong base of an alkali or alkaline-earth metal other than Cs or Rb (called normal base) is such that the molar ratio of normal base/(cesium, rubidium or quaternary phosphonium hydroxide and/or salt) is higher than or equal to 1 and preferably between 2 and 10 in the case of a cesium hydroxide or fluorine-free salt, and between 5 and 15 in the case of a quaternary phosphonium hydroxide or salt.

The invention has made it possible to establish that the fluoride anion is far from being necessary for the improvement in the output efficiency and selectivity of the PDOS depolymerization and cyclization reactions, and that the presence of cations, especially monovalent ones, of large size (larger than that of potassium) and which are stable at the reaction temperatures, such as cesium or quaternary phosphonium, plays an important part in this process.

The polymers used as substrate in the depolymerization reaction according to the invention are conventionally PDOS mixtures in which the number of silicon atoms in the chain is generally of the order of 5 to 100, and especially those obtained during the hydrolysis of the chlorosilanes employed as in the industrial process for the manufacture of silicones. These polymers may be more particularly polydimethylsiloxanes, but also include polymethylvinylsiloxanes and fluorine-containing PDOSs as well as other PDOSs such as polydiethyl- or polymethylphenylsiloxanes, to the exclusion of the siloxyl units substituted by hydrogen, of the $\equiv$Si—H type.

The process according to the invention may be conducted at a relatively low temperature, generally lower than 200° C., preferably between 110° and 150° C.

Other advantages and characteristics of the invention will appear in the following description, given by way of a nonlimiting example, of tests employing initiators of the prior art and initiators (metal derivative(s) with optional base).

EXAMPLE 1

In this example, the starting PDOS employed is a mixture made up of 90% by weight of an α,ω-dihydroxyl-containing linear polydimethylsiloxane (PDMS) $HO(SiMe_2O)_nH$, in which the mean n is 40, and of 10% by weight of cyclic PDMSs.

Its number-average molecular mass is close to 3000 g/mol.

The reaction mass containing all the reactants, namely 116 g of the starting PDOS and the quantities of initiators which are shown in Table I, given below, is introduced into a reactor of 500 ml volume.

The reaction mixture is stirred by means of a bladed stirrer and heated using a thermostated oil bath up to a temperature of approximately 135° C.

The reaction mixture present in the reactor is fed continuously with PDOS preheated to approximately 130° C. and present in a graduated funnel 200 ml in capacity and heated by a jacket. The rate of flow of the PDOS present in the feed funnel into the reaction mixture is controlled by means of a control valve. The flow rate from the funnel is preferably adjusted to the flow rate of the distillation in such a way that the level of the reaction mixture in the boiler is kept at a constant level.

The reaction products are distilled at a reduced pressure of 4800 Pa.

The vapours are condensed in a condenser and the distillate is isolated in a graduated receiver.

This experimental device makes it possible to determine the output efficiency or flow rate of cyclic PDMS per unit volume for a given initiator.

Table I, below, illustrates the output efficiency obtained during tests performed by following the experimental scheme defined above.

The figures given in the OUTPUT EFFICIENCY column include the quantity of cyclic PDMS present in the starting PDOS and the quantity actually formed by depolymerization, this latter quantity representing approximately 90% of the total output efficiency appearing in the table.

TABLE I

| TEST | INITIATOR | TEMPERATURE (°C.) | OUTPUT EFFICIENCY (ml/h) |
|---|---|---|---|
| A (control) | KOH (3 g, 54 mmol) | 138 | 240 |

TABLE I-continued

| TEST | INITIATOR | TEMPERATURE (°C.) | OUTPUT EFFICIENCY (ml/h) |
|---|---|---|---|
| B (according to the invention) | KOH (3 g, 54 mmol) $(C_6H_5)_4PBr$ (2.1 g, 5 mmol) | 132 | 360 |

When tests A and B are compared it is found that an acceleration in the depolymerization of the PDOSs is produced when the potassium hydroxide and the quaternary phosphonium halide are used in association, despite a lower reaction temperature.

EXAMPLE 2

In this example, the starting material is a PDOS which is a mixture of 63% by weight of a linear PDMS of the $HO(SiMe_2O)_nH$ type of mean n of 57 with 37% of cyclic PDMS. Its number-average molecular mass is close to 4000 g/mol.

The procedure follows the same scheme as that described in Example 1.

113.5 g of this mixture and the quantities of initiators which are shown in Tables II and III, given below, are introduced into the reactor. The reaction mixture is then heated to approximately 132° C. by means of a thermostated oil bath.

The mixture is kept at a constant volume by continuous feeding of mixture preheated to 130° C.

The cyclic PDMSs are distilled at reduced pressure (4800 Pa).

Analysis by gas phase chromatography (GC) shows that the cyclic PDMSs contain approximately 70% by weight of $D_4$ and 20% of $D_5$. The reining 10% consists of lower oligomers of $D_3$ type or higher ones.

Table II, below, illustrates the output efficiency per unit volume obtained during 3 tests performed while following the experimental scheme of example 2. It will be understood that the quantity of cyclic PDMS actually formed by depolymerization represents here approximately 100−37=63% of the total output efficiency appearing in the table.

TABLE II

| TEST | INITIATOR | OUTPUT EFFICIENCY AT 132° C. (ml/h) |
|---|---|---|
| C (control) | KOH (3.1 g; 55 mmol) | 180 |
| D (control) | KOH (4.51 g; 80 mmol) | 230 |
| E (according to the invention) | KOH (3.32 g; 59 mmol) CsCl (1.32 g; 7.7 mmol) | 330 |

It is found that, as in Example 1, the use of an initiator according to the invention, using potassium hydroxide and cesium chloride in association, permits an acceleration of the depolymerization.

Table III shows the effect of the use of an initiator according to the invention, using potassium hydroxide in association with cesium acetate, on the improvement in the quality of the cyclic PDMS mixture.

TABLE III

| TEST | INITIATOR | CONCENTRATION OF D3 IN THE MIXTURE OF CYCLOSILOXANES (w/w) (*) |
|---|---|---|
| F (control) | KOH (2.6 g; 46 mmol) | 8.2% |
| G (according to the invention) | KOH (2.5 g; 45 mmol) CsOAc (1.7 g; 9 mmol) | 6.3% |

(*) Result obtained by GPC chromatography.

It is found that the use of the cesium acetate coinitiator jointly with the potassium hydroxide permits a gain in quality by decreasing the hexamethylcyclotrisiloxane concentration of the order of 2% by weight.

EXAMPLE 3

The procedure follows the same scheme as in Example 1, while replacing the KOH base with CsOH without another constituent. The result of the test carried out is given in Table IV.

TABLE IV

| TEST | INITIATOR | T° (°C.) | OUTPUT EFFICIENCY (ml/h) |
|---|---|---|---|
| H (according to the invention) | CsOH (6.9 g; 46 mmol) | 125.5 | 400 |

When test A in Table I is compared with this test it is found that the replacement of potassium hydroxide (KOH) with cesium hydroxide enables a large gain in output efficiency to be obtained.

Furthermore, analysis of the reaction products shows that the percentage of the three-dimensional groups remains extremely low and generally does not exceed 0.05% by weight.

EXAMPLE 4

The procedure follows the same scheme as in Example 2. The configuration of the tests and the results obtained are collated in Table V, which follows:

TABLE V

| TEST | INITIATOR | T (°C.) | OUTPUT EFFICIENCY (ml/h) |
|---|---|---|---|
| I (control) | KOH (1.5 g; 27 mmol) | 132 | 120 |
| J (according to the invention) | KOH (1.5 g; 27 mmol) CsOH (1.4 g; 9 mmol) | 124 | 125 |

It is found that, when proceeding according to the invention, an equivalent output efficiency is obtained while working at a lower temperature (8° C. less).

We claim:

1. A process for the manufacture of cyclic polydiorganosiloxanes comprising depolymerizing a polydiorganosiloxane in the presence of an initiator which comprises a cesium, rubidium or quaternary phosphonium hydroxide, or a combination of a fluorine-free cesium, fluorine-free rubidium or quaternary phosphonium salt and a hydroxyl containing base of an alkali or alkaline-earth metal other than cesium or rubidium, or mixtures thereof.

2. The process according to claim 1, wherein said initiator comprises cesium hydroxide, rubidium hydroxide or quaternary phosphonium hydroxide and a hydroxyl containing base of an alkali or alkaline-earth metal other than cesium or rubidium.

3. The process according to claim 1, wherein said initiator is a fluorine-free cesium salt, fluorine-free rubidium salt or quaternary phosphonium salt and said initiator further comprises a hydroxyl-containing base of an alkali or alkaline-earth metal other than cesium or rubidium.

4. The process according to claim 1, wherein said cyclic polydiorganosiloxane is octamethylcyclotetrasiloxane.

5. The process according to claim 1, wherein said cyclic polydiorganosiloxane is decamethyl cyclopentasiloxane.

6. The process according to claim 1 wherein said initiator comprises a fluorine-free cesium or rubidium halide.

7. The process according to claim 6, wherein the fluorine-free halide is a chloride or a bromide.

8. The process according to claim 1, wherein said initiator comprises a fluorine-free cesium or rubidium salt.

9. The process according to claim 8, wherein said salt is a carbonate, carboxylate, phosphate, nitrate or sulphate.

10. The process according to claim 1, wherein the initiator comprises a fluorine-free cesium salt.

11. The process according to claim 10, wherein said cesium salt is a carboxylate chloride or bromide.

12. The process according to claim 1, wherein the initiator comprises a quaternary phosphonium compound with a cationic part that corresponds to the formula (I):

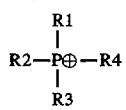

(I)

in which the groups R1, R2, R3 and R4 denote identical or different optionally substituted hydrocarbon radicals whose free valency is carried by a carbon atom.

13. The process according to claim 12, wherein R1, R2, R3 and R4 denote identical or different linear or branched alkyl, cycloalkyl or aromatic radicals.

14. The process according to claim 13, wherein at least one of said radicals R1, R2, R3 and R4 is an aryl radical.

15. The process according to claim 13, wherein at least one of said radicals R1, R2, R3 and R4 is substituted by at least one halogen atom, $NO_2$ or CN.

16. The process according to claim 13, wherein the total number of carbon atoms carried by the said radicals is less than or equal to 50.

17. The process according to claim 16, wherein the total number of carbon atoms is between 6 and 30.

18. The process according to claim 1, wherein said compound comprises a quaternary phosphonium halide.

19. The process according to claim 18, wherein said quaternary phosphonium salt is a chloride or bromide.

20. The process according to claim 1, wherein said initiator further comprises potassium hydroxide, sodium hydroxide, lithium hydroxide or mixtures thereof.

21. The process according to claim 1, wherein the quantity of cesium, rubidium or quaternary phosphonium hydroxide per 100 g of starting polydiorganosiloxane is from 3 to 100 mmol.

22. The process according to claim 1, wherein the quantity of cesium, rubidium or quaternary phosphonium hydroxide and/or salt per 100 g of starting polydiorganosiloxane is between 3 and 50 mmol; the molar ratio of hydroxyl containing base to cesium, rubidium or quaternary phosphonium hydroxide and/or salt is higher than or equal to 1 when a cesium hydroxide or fluorine-free salt is employed; and the molar ratio of hydroxyl containing base to cesium, rubidium or quaternary phosphonium hydroxide and/or salt is between 5 and 15 when a quaternary phosphonium hydroxide or salt is employed.

23. The process according to claim 1, wherein the depolymerization temperature is lower than 200° C.

24. The process according to claim 22, wherein the depolymerization temperature is from 110° to 150° C.

25. A process for the manufacture of cyclic polydiorganosiloxanes comprising deploymerizing a polydiorganosiloxane in the presence of an initiator which comprises cesium, rubidium, a quaternary phosphonium hydroxide or mixtures thereof, with the proviso that cesium hydroxide is not the sole initiator.

26. A process for the manufacture of cyclic polydiorganosiloxanes comprising depolymerizing a polydiorganosiloxanes in the presence of a reaction mass which consists essentially of cyclic polydiorganosiloxane and a cesium hydroxide initiator.

* * * * *